United States Patent [19]
Winston

[11] Patent Number: 5,135,528
[45] Date of Patent: Aug. 4, 1992

[54] HOCKEY STICK CHISEL

[76] Inventor: Frederick Winston, 12087 Sheraton Ln., Cincinnati, Ohio 45246

[21] Appl. No.: 710,326

[22] Filed: Jun. 4, 1991

[51] Int. Cl.$^5$ .............................................. A61B 17/00
[52] U.S. Cl. ........................................ 606/79; 606/84
[58] Field of Search ................ 606/79, 84, 85, 184, 606/185, 186; 30/314, 167, 167.1, DIG. 8

[56] References Cited

U.S. PATENT DOCUMENTS

| | | | |
|---|---|---|---|
| 2,876,777 | 3/1959 | Kees, Jr. | 606/84 |
| 4,239,045 | 12/1980 | Schlein | 606/84 |
| 4,686,978 | 8/1987 | Wadeworth | 606/84 |
| 4,985,035 | 1/1991 | Torre | 606/84 |
| 5,013,314 | 5/1991 | Firica | 606/84 |

FOREIGN PATENT DOCUMENTS

| | | | |
|---|---|---|---|
| 1082411 | 3/1984 | U.S.S.R. | 606/84 |
| 1162415 | 6/1985 | U.S.S.R. | 606/84 |

Primary Examiner—Michael A. Brown
Attorney, Agent, or Firm—Wood, Herron & Evans

[57] ABSTRACT

A medical instrument for performing a vertebral osteotomy comprising an elongated handle member having first and second ends and a curved blade member extending from the second end of the handle, which curved blade member terminates in a chisel at a forward edge. The forward tip of the chisel is chamfered so as to safeguard against contacting the spinal cord during the vertebral osteotomy.

10 Claims, 1 Drawing Sheet

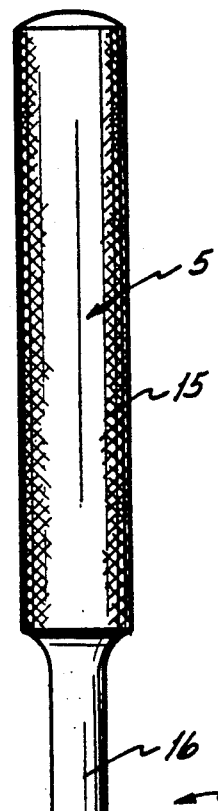
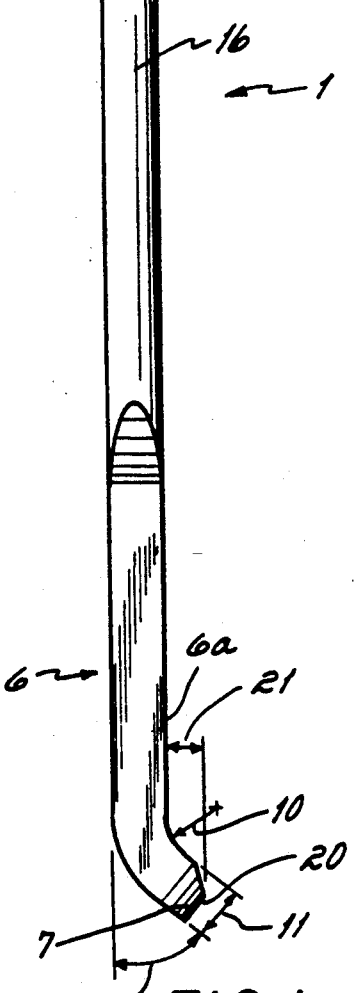
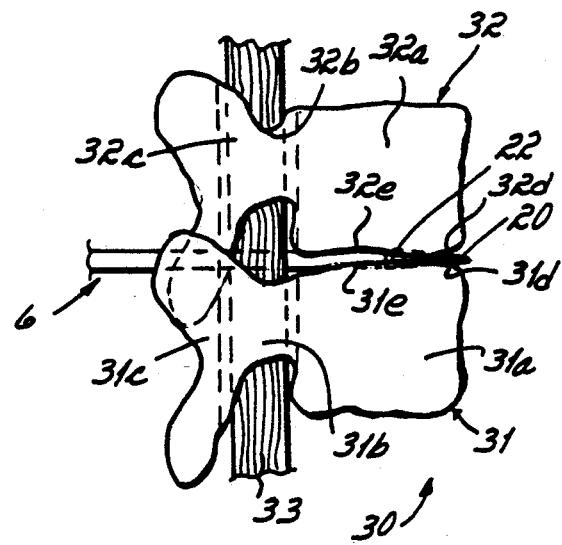
FIG. 3
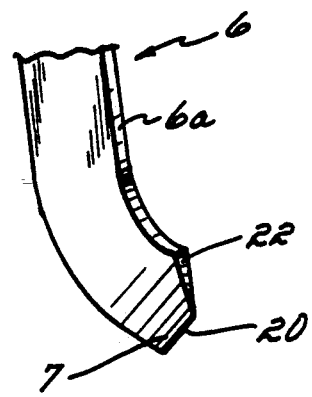
FIG. 2
FIG. 1

HOCKEY STICK CHISEL

FIELD OF THE INVENTION

This invention relates to medical instruments, and more particularly to a medical instrument for use during a vertebral osteotomy.

BACKGROUND OF THE INVENTION

Back surgery, and particularly the vertebral osteotomy procedure, has heretofore been difficult and cumbersome to perform due to the geometry of the operative site. Specifically, the operative site comprises a spinal cord and a plurality of vertebrae surrounding the spinal cord along its length. In a vertebral osteotomy, facing sides of the bodies of two adjacent vertebrae are trimmed or otherwise cut away. Difficulties are encountered, however, as the bone which is cut away from the vertebral body is located anterior of the spinal cord. It will be appreciated that a surgeon's vision or line of sight is impaired in this type of procedure, since in a vertebral osteotomy the patient lies prone, and this causes the spinal cord to block the view of that portion of the vertebral body which is sought to be cut or trimmed away.

Further complicating the vertebral osteotomy is the fact that a sharpened cutting instrument or chisel, known as an osteotome, must be utilized to cut or otherwise trim away portions of the bony vertebral body. However, such trimming and cutting takes place in the vicinity of the delicate spinal cord, which lies in a canal formed by the vertebral bodies, pedicles, and laminae.

SUMMARY OF THE INVENTION

It has therefore been one objective of the present invention to provide a medical instrument wherein a vertebral osteotomy is facilitated when the vertebral bone which is sought to be cut away is located anterior of a patient's spinal cord.

It has been another objective of the present invention to provide a medical instrument wherein the vertebral bone is sought to be cut away is located anterior of a patient's spinal cord and which safeguards against coming in contact with the spinal cord.

The present invention is a medical instrument for performing a vertebral osteotomy comprising an elongated handle member having first and second ends and a curved blade member extending from the second end of the handle, which curved blade member terminates in a chisel at a forward edge thereof. The forward tip of the chisel is chamfered so as to safeguard against contacting the spinal cord.

One advantage of the present invention is that a vertebral osteotomy is facilitated wherein the bony portion of the vertebral body which is sought to be removed is located anterior of the spinal cord.

Another advantage of the present invention is that a medical instrument has been provided which during a vertebral osteotomy safeguards against contacting the spinal cord.

These and other objects and advantages of the present invention will become more readily apparent during the following detailed description taken in conjunction with the drawings herein, in which:

BRIEF DESCRIPTION OF THE DRAWINGS

FIG. 1 is a perspective view of the medical instrument of the present invention;

FIG. 2 is an enlarged view of the chisel of the medical instrument of the present invention; and FIG. 3 is an illustration of the use of the medical instrument of the present invention.

DESCRIPTION OF THE PREFERRED EMBODIMENTS

With reference to FIG. 1, there is illustrated the medical instrument of the present invention, or so-called hockey stick chisel 1. The hockey stick chisel 1 is preferably fabricated of high grade stainless steel and comprises, generally, an elongated handle member 5, a planar curved blade member 6 extending from the lower end of the handle 5, and a sharpened tip or chisel 7.

The handle 5 includes an upper cylindrical grasping portion 15 and a lower necked-down portion 16 which connects the grasping portion 15 with the curved blade member 6.

As shown in FIG. 1, curved blade member 6 has a radius of curvature 10 which ranges between about 0.2 inches and about 0.5 inches, and which, preferably, is about 0.31 inches. The curved blade member 6 has a width 11 which ranges between about 0.2 inches and about 0.5 inches, and which ideally is equal to about 0.31 inches. The curved blade member 6 is oriented with respect to the handle member 5 at an angle 12 which ranges between about 30° and 70°, and which preferably is about 45°.

Chisel 7 has a bone cutting edge 20 formed by beveling both sides of thee curved blade member 6. This chisel 7 extends about 0.2 inches to 0.4 inches, and preferably about 0.31 inches, from the forward edge 6a of the blade member 6 as illustrated at 21. The chisel 7 has a chamfered non-cutting edge 22 (FIG. 2), thereby eliminating what would be the forward tip of the chisel 7.

With reference to FIG. 3, there will be seen the hockey stick chisel 1 of the present invention as utilized during a vertebral osteotomy. For this procedure, the operative sight 30 includes adjacent vertebrae 31 and 32 which comprise, respectively, body 31a, pedicle 31b and lamina 31c, and body 32a, pedicle 32b and lamina 32c. Spinal cord 33 lies in the canal formed by the vertebral bodies 31a and 32a, pedicles 31b and 32b, and laminae 31c and 32c. Vertebral rims 31d and 32d, which are sought to be removed during a vertebral osteotomy, appear on facing sides 31e and 32e of the adjacent vertebral bodies 31a and 32a.

To perform the vertebral osteotomy, the operative sight 30 is first exposed. Then the curved blade member 6 is inserted between bodies 31a and 32a of vertebrae 31 and 32. The chisel 7 is then worked into the gap between facing sides 31e and 32e of vertebrae 31 and 32. The chisel edge 20 of the chisel 7 is then employed to slice or cut away the vertebral rims 31d and 32d on the facing sides 31e and 32e of the adjacent vertebral bodies 31a and 32a.

The instrument 1 is advantageously designed to facilitate the vertebral osteotomy. The width 11 of the curved blade member 6 in conjunction with the angle 12 which this curved blade member 6 is oriented with respect to the handle 5 allows for the trimming away of vertebral rims 31d and 32d. The dimension 21 by which the chisel edge 20 extends from the forward edge 6a of the curved blade member 6 additionally facilitates the trimming and cutting away of the vertebral rims 31d and 32d. And, the bevel 22 on the chisel 7 safeguards against the instrument 1 contacting the spinal cord 33.

Those skilled in the art will readily recognize adaptations and modifications which can be made to the medical instrument of the present invention which result in an improved medical instrument yet without departing from the spirit or scope of the present invention. Accordingly, I intend to be limited only by the broad scope of the appended claims.

What is claimed is:

1. A medical instrument for performing a vertebral osteotomy comprising:
    an elongated handle member having first and second ends, and
    a planar curved blade member extending from said second end of said handle and adapted to be inserted between adjacent vertebrae, said curved blade member terminating in a chisel at a forward edge thereof, said chisel having a chamfered non-cutting edge extending generally from said forward edge to an inner side of said chisel.
2. The medical instrument of claim 1 wherein said curved blade member tapers gradually to said chisel.
3. The medical instrument of claim 2 wherein said curved blade member has a radius of curvature of about 0.31 inches.
4. The medical instrument of claim 2 wherein said curved blade member has a radius of curvature ranging from about 0.2 inches to about 0.5 inches.
5. The medical instrument of claim 4 wherein said curved blade member has a width dimension ranging from about 0.2 inches to about 0.5 inches.
6. The medical instrument of claim 5 wherein said curved blade member is oriented with respect to said handle member at an angle ranging between about 30° and about 70°.
7. The medical instrument of claim 6 wherein a forward tip of said chisel extends from said blade member in an amount ranging from about 0.2 inches to about 0.4 inches.
8. The medical instrument of claim 5 wherein said curved blade member is oriented with respect to said handle member at an angle of about 45°.
9. The medical instrument of claim 6 wherein a forward tip of said chisel extends from said blade member by about 0.31 inches.
10. The medical instrument of claim 4 wherein said curved blade member has a width dimension of about 0.31 inches.

* * * * *